United States Patent
Joannet et al.

(10) Patent No.: US 7,541,501 B2
(45) Date of Patent: Jun. 2, 2009

(54) PROCESS FOR THE PREPARATION OF 2-BUTENE-1,4-DIOL

(75) Inventors: Eric Joannet, Moudon (CH); Lioubov Kiwi-Minsker, Préverenges (CH); Albert Renken, St. Sulpice (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 11/794,240

(22) PCT Filed: Dec. 29, 2005

(86) PCT No.: PCT/EP2005/014103

§ 371 (c)(1),
(2), (4) Date: Mar. 17, 2008

(87) PCT Pub. No.: WO2006/072441

PCT Pub. Date: Jul. 13, 2006

(65) Prior Publication Data

US 2008/0312475 A1  Dec. 18, 2008

(30) Foreign Application Priority Data

Jan. 7, 2005  (EP)  ................. 05000227

(51) Int. Cl.
C07C 31/18 (2006.01)
C07C 29/17 (2006.01)

(52) U.S. Cl. ....................... 568/857; 568/861

(58) Field of Classification Search ................ 568/857, 568/861

See application file for complete search history.

(56) References Cited

OTHER PUBLICATIONS

L. Kiwi-Minsker et al., "Loop reactor staged with structured fibrous catalytic layers for liquid-phase hydrogenations", Chemical Engineering Science, vol. 59, No. 22-23, Nov. 2004, pp. 4919-4925.
E. Joannet et al., "Palladium supported on filamentous active carbon as effective catalyst for liquid-phase hydrogenation of 2-butyne-1,4-diol to 2-butene-1,4-diol", Chemical Engineering Science, vol. 57, No. 16, Aug. 2002, pp. 3453-3460.
L. Kiwi-Minsker et al., "Solvent-Free Selective Hydrogenation of 2-Butyne-1,4-diol over Structured Palladium Catalyst", Industrial & Engineering Chemistry Research, vol. 44, No. 16, 2005, pp. 6148-6153.
R. Xavier et al., "Polymer-Supported Palladium and Platinum Species as Hydrogenation Catalysts", Journal of Polymer Science, Part A: Polymer Chemistry, vol. 30, No. 13, 1992, pp. 2665-2676.

*Primary Examiner*—Sikarl A Witherspoon
(74) *Attorney, Agent, or Firm*—Nixon & Vanderhye PC

(57) ABSTRACT

2-Butene-1.4-diol can be prepared by hydrogenating 2-butyne-1,4-diol in the presence of a structured catalyst in the absence of a solvent.

11 Claims, 3 Drawing Sheets

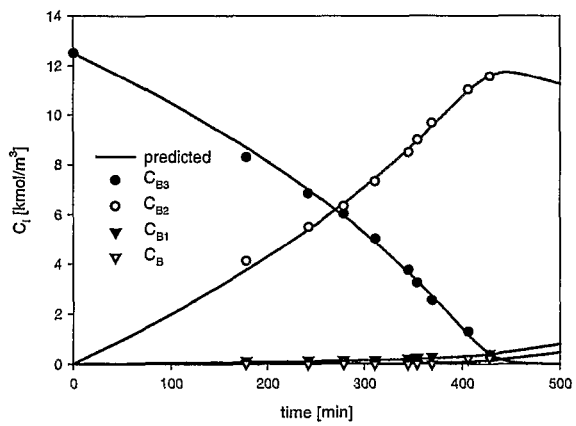
Figure 1: Measured and predicted reactant and product concentration as function of time. Solvent free hydrogenation; catalyst mass: 4.6mg Pd; temperature: 352K; hydrogen pressure: 1.5 MPa.
$C_B$ concentration of butanol
$C_{B1}$ concentration of butanediol
$C_{B2}$ concentration of butenediol
$C_{B3}$ concentration of butynediol

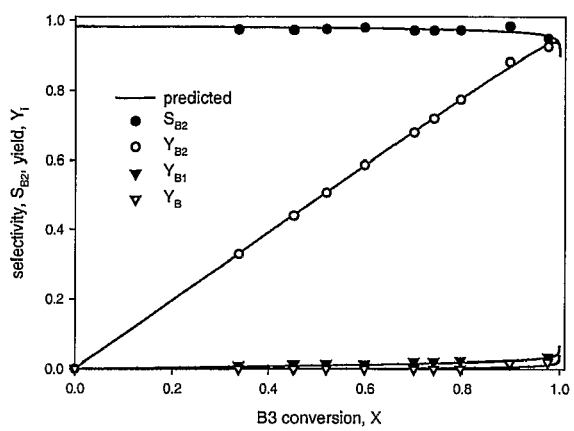
Figure 2 : Measured and predicted yield and selectivity towards butenediol as function of butynediol conversion (conditions see Fig. 1)
$Y_B$ yield of butanol
$Y_{B1}$ yield of butanediol
$Y_{B2}$ yield of butenediol
$S_{B2}$ selectivity for butynediol

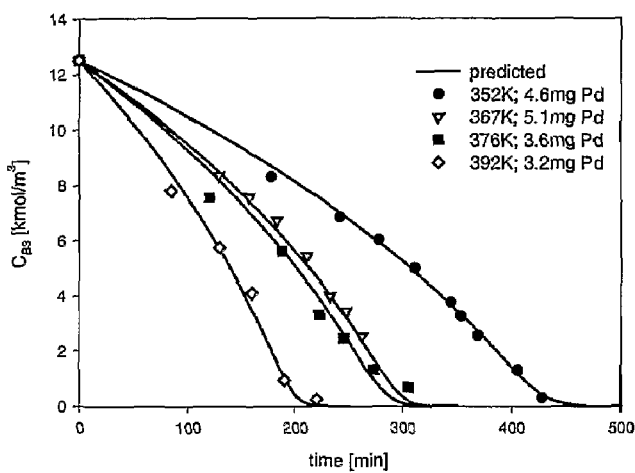
Figure 3 : Measured and predicted reactant concentration as function of time and temperature. Solvent free hydrogenation. Hydrogen pressure: 1.5 MPa

PROCESS FOR THE PREPARATION OF 2-BUTENE-1,4-DIOL

This application is the U.S. national phase of international application PCT/EP2005/014103 filed 29 Dec. 2005 which designated the U.S. and claims benefit of EP 05000227.8, dated 7 Jan. 2005, the entire content of which is hereby incorporated by reference.

The present invention relates to the preparation of 2-butene-2.4-diol, which is an important industrial intermediate in the preparation of vitamin $B_6$, pharmaceuticals and insecticides.

2-butene-1,4-diol is usually prepared by catalytic hydrogenation of 2-butyne-1,4-diol in a solvent, e.g., in an aqueous solution. In order to facilitate recovery of the catalyst it has been proposed to use filamentous woven cloths as a carrier for the catalyst in the hydrogenation of aqueous solutions of 2-butyne-1,4-diol, see *Chem. Engineering Science* 57 (2002), 3453-3460.

According the present invention it has now been found that 2-butene-1,4-diol can be prepared in high yield and selectivity by catalytic hydrogenation of 2-butyne-1,4-diol over a structured catalyst in the absence of a solvent. Since hydrogen is sparingly soluble in solvents such as water the absence of such solvents increases the economy of the hydrogenation process in that it results in higher turnover per time unit. Further, the process of the present invention by avoiding separation and recycling of a solvent is preferred for reasons of environmental protection.

Accordingly, the present invention relates to a process for the preparation of 2-butene-1.4-diol which comprises hydrogenating 2-butyne-1,4-diol in the presence of a structured catalyst and in the absence of a solvent.

The term "structured catalyst" as used herein refers to catalysts wherein the spatial position of the catalyst is controlled. Structured catalysts are known in the art, see, e.g., *Chimia* 56(4), 2002, 159-163. Examples of structured catalysts are ceramic carrier constructions and fibrous structures, especially filamentous woven cloths. All types of filamentous woven cloths can be used for use in the present invention. The fibers may be from organic or inorganic matter. Examples are fabrics from activated carbon fibers such as acrylonitril fibers, glass fibers, ceramic fibers, metal fibers or fleece composite oxides of activated carbon fibers. Preferred are polyacrylonitril fabrics. The individual fibers of the filamentous woven cloth preferably have a diameter of about 2 μm to about 100 μm, especially a diameter of no more than about 20 μm. The fabrics are suitably be woven from threads consisting of a boundle of individual fibers, providing a porous size of the woven cloth of less than about 1 mm. They may be chemically treated, e.g., with nitric acid to modify the specific surface and may have a coating, e.g. of metals such as Al, Ti or Pb to improve selectivity.

As the catalyst, every hydrogenation catalyst which catalyzes the selective hydrogenation of 2-butyne-2,4-diol to 2-butene-2,4-diol can be used. Examples of such catalysts are noble metals such as palladium, platinum, iridium, rhodium, ruthenium or combinations thereof. The catalyst may be present on the carrier fabric in an amount up to about 10 mass %, suitably 1-10 mass %. The loading of the carrier fabric is accomplished by treating with a solution of a precursor of the catalyst, e.g. a salt of the catalyst metal and subsequent drying and heating in a hydrogen atmosphere and can be controlled by the concentration of the catalyst precursor in the loading solution.

The hydrogenation in accordance with the present invention can be carried out under conditions conventionally used for hydrogenations of 2-butin-2,4-diol to produce 2-butene-2,4-diol. Suitably, the hydrogenation is carried out at a pressure of about 0.1 to about 6 MPa and at a temperature of about 350K to about 500K. The hydrogenation can be carried out batch wise or in continuous mode.

The following Example illustrates the invention further without limiting it.

EXAMPLE

Catalyst Preparation

Activated carbon fibres of polyacrylonitrile origin in the form of plain woven fabrics (Taiwan Carbon Technology Co) were used as supports for catalyst preparation. The fabrics are woven from the long threads of ca. 0.5 mm in diameter. These threads consist of a bundle of elementary filaments of 3-5 μm. The palladium deposition on the fabric was carried out via ion-exchange from aqueous solution of $Na_2PdCl_4$ as described in *Chem. Eng. Sci.* 2002, 57, 3453-3460. The loading of palladium was 4 mass % as determined by atomic absorption spectroscopy, and the catalysts were characterized via BET-method for specific surface area and pore size distribution. Pulse chemisorption of carbon monoxide was applied for the determination of Pd dispersion, see *Chem. Eng. Sci.*, supra.

Experimental Set-Up

The experimental set-up is described in detail in *Chem. Eng. Sci.*, supra.

The reaction was carried out in a batch reactor (150 ml autoclave, Buechiglas, Uster, CH), at isothermal conditions kept by a heating jacket. The autoclave was provided with a quantitative gas supply system.

The fibrous catalysts were placed between two metal gauzes (20×40 mm) fixed on the stirrer. The amount of catalyst placed in the reactor was varied between 150 and 35 mg. The agitation speed was kept at 1500 rpm to avoid mass transfer limitations. To achieve an efficient gas-liquid contact a self-gassing hollow shaft stirrer was used. The autoclave was fed with hydrogen (>99.99%) under isobaric reaction conditions.

Pure 2-butyne-1,4-diol was charged as a solid (mp 331K) and molten under Argon to prevent degradation of the reactant. After the required temperature was reached, the reactor was flushed with hydrogen and pressurized to the desired level. During the course of the reaction, the pressure of $H_2$ in the reactor was maintained constant by supplying hydrogen from the reservoir at the rate of consumption. The pressure in the $H_2$ reservoir was monitored continuously allowing in situ measurement of the instantaneous hydrogen consumption.

Samples of liquids withdrawn from the loop are analysed by gas chromatography (Auto System XL, PERKIN ELMER) with He as a carrier gas and a FID-detector. Product separation was performed on a 30 m Perkin Elmer Elite Series 0.25 mm capillary column with a 0.25 micron coating, at temperature ramp of 20 K/min from 373 to 493K. Butan-1,3-diol was used as internal standard for quantitative GC analysis.

The results of experiments under varying reaction conditions can be seen from FIGS. 1 to 3.

FIG. 1 shows typical concentration time profiles for a reaction temperature of 352K. The measured and predicted selectivity for butenediol ($B_2$) is ca. 98% up to butynediol ($B_3$) conversions of 90% and drops to 95% at 99% conversion as shown in FIG. 2. The influence of temperature on the rate of reaction can be seen from FIG. 3, where the reactant concentration is shown as function of time. Based on the initial reaction rate, the dependence of the turnover frequency on temperature can be calculated.

What is claimed is:

1. Process for the preparation of 2-butene-1,4-diol which comprises hydrogenating 2- butyne-1,4-diol in the presence of a structured catalyst and in the absence of a solvent.

2. A process as in claim 1 wherein the structured catalyst support is a filamentous woven cloth.

3. A process as in claim 2 wherein filamentous woven cloth is made of activated carbon fibers.

4. A process as in claim 2 the activated carbon fibers are made from polyacrylonitril fibers.

5. A process as in claim 2 wherein the fibers have a diameter of about 2 μm to about 100 μm.

6. A process as in claim 2 wherein the fibers have a diameter of no more than 20 μm.

7. A process as in claim 2 wherein the porous size of the woven cloth is less than 1 mm.

8. A process as in claim 2 wherein the catalyst metal is a palladium catalyst.

9. A process as in claim 1 wherein the catalyst loading of the carrier is about 1 to about 10 mass %.

10. A process as in claim 1 wherein the hydrogenation is carried out at a pressure of about 0.1 to about 6 MPa.

11. A process as in claim 1 wherein the hydrogenation is carried out at a temperature of about 350K to about 500K.

* * * * *